United States Patent [19]
Olichney

[11] Patent Number: 5,082,014
[45] Date of Patent: Jan. 21, 1992

[54] SOLUTION PUMPING SYSTEM INCLUDING DISPOSABLE PUMP CASSETTE

[75] Inventor: Michael D. Olichney, Boulder, Colo.

[73] Assignee: Abbott Laboratories, Abbott Park, Ill.

[21] Appl. No.: 444,487

[22] Filed: Dec. 1, 1989

[51] Int. Cl.$^5$ .............................................. E03B 7/07
[52] U.S. Cl. ........................................ 137/1; 137/563; 137/565
[58] Field of Search ................... 137/563, 565, 1, 363; 417/434, 435, 502, 503

[56] References Cited

U.S. PATENT DOCUMENTS

| | | | |
|---|---|---|---|
| 3,190,321 | 6/1965 | Robinson | 137/563 |
| 3,913,606 | 10/1975 | Anderson, Jr. | 137/563 |
| 4,479,761 | 10/1984 | Bilstad et al. | 417/395 |
| 4,563,173 | 1/1986 | Ledley | 137/565 |
| 4,818,186 | 4/1989 | Pastrone et al. | 417/63 |
| 4,842,584 | 6/1989 | Pastrone | 604/50 |

Primary Examiner—A. Michael Chambers
Attorney, Agent, or Firm—A. Nicholas Trausch

[57] ABSTRACT

An apparatus and method are disclosed for effecting compounding of parenteral admixture solutions, and recirculation with the admixture solution being formed. The apparatus includes a pump cassette configured for operative association with a pump driver, whereby one or more selected source solutions are delivered through the pump cassette to an associated admixture container. After pumping of each source solution, the present method contemplates that the admixture being formed is recirculated through the pump cassette, thereby diluting any source solution in the cassette and associated tubing. In this manner, the possible mixture of incompatible source solutions, resulting in formation of precipitate, is desirably avoided.

9 Claims, 1 Drawing Sheet

SOLUTION PUMPING SYSTEM INCLUDING DISPOSABLE PUMP CASSETTE

TECHNICAL FIELD

The present invention generally relates to arrangements for preparing patient parenteral solutions, and more particularly to a solution compounding apparatus including a pump cassette and tubing arrangement for compounding a parenteral admixture, and for effecting dilution of a source solution in the pump cassette by recirculation of the admixture.

BACKGROUND OF THE INVENTION

Modern patient health care routinely requires the preparation of very large numbers of parenteral solutions for intravenous or intramuscular administration to patients. Such parenteral solutions include those formulated for nutritional purposes, as well as drug-containing admixtures for therapeutic purposes.

In view of the large number of such admixtures which must be prepared on a routine basis, efficient and accurate preparation of such solutions is highly desirable. In the past, preparation of such solutions has typically been effected manually by the pharmacist and assisting personnel in a health care facility. Specifically, an appropriate intravenous solution container, typically comprising a flexible patient bag, is selected, with the container typically being partially empty, or containing appropriate base nutritional solutions or diluents. The pharmacist or other personnel then calculates the amounts of various liquid components that need to be made to the solution container in accordance with the physician's order. These components are then measured by drawing them into syringes of the appropriate sizes, with the contents of the syringes then injected into the final solution container.

As will be appreciated, accurate preparation of parenteral solutions in this manner is time consuming, with the manual nature of the procedure raising the possibility of error in the preparation of the resultant admixtures. Additionally, the repeated needle-puncturing in additions of solutions to the admixture container increase the risk of contamination.

Accordingly, automatic systems for compounding parenteral admixtures are coming into increasingly widespread use. Such systems typically include arrangements for measuring and combining one or more selected source solutions in a suitable admixture container for subsequent patient administration. Such devices ordinarily include programmable controls as well as suitable monitoring devices to greatly facilitate efficient and accurate preparation of parente..i admixtures.

The present invention relates to an admixture compounding apparatus for use in association with an automated compounding system. In particular, the present apparatus, and method of use thereof, is specifically configured to avoid mixture of potentially incompatible source solutions, which in their relatively undiluted and concentrated state could undesirably form precipitates.

SUMMARY OF THE INVENTION

The present admixture compounding apparatus, and method of use, is particularly configured to avoid mixture of potentially incompatible source solutions. This desirable result is achieved by recirculation of the admixture being formed so it functions as a diluent during use of the apparatus. In this manner, formation of a precipitate by potentially incompatible source solutions is desirably avoided.

The present apparatus includes a pump cassette for use in association with a pump driver of a compounding system. The pump cassette functions as a disposable interface between the source solutions to be combined and the pump driver, and is essentially a self-contained arrangement which is the only part of the compounding system, together with the associated tubing, with which the various source solutions and the resultant admixture come into contact.

As such, the pump cassette includes a plurality of liquid inlets, a liquid outlet, and a liquid flow path joining the inlets and outlet in fluid communication. The pump cassette further includes a self-contained positive displacement pump for pumping liquid from a selected one of the inlets to the outlet. The structure of the cassette is provided by a rigid cassette body, within which an elastomeric diaphragm is positioned. The diaphragm and cassette body together define the required inlets, outlet, flow path, and liquid pump. The pump cassette cooperates with the associated pump driver such that the pump driver operates the positive displacement pump, and further selectively opens and closes the various liquid inlets and outlet for effecting flow control within the pump cassette.

In accordance with the present invention, an admixture container is provided for receiving at least one source solution from the pump cassette for forming an admixture solution therein. In the illustrated embodiment, the admixture container comprises a flexible patient bag typically employed for preparation and administration of parenteral solutions.

The present apparatus further includes a tubing arrangement for effecting the desired solution compounding in the admixture container, and dilution of any source solution in the pump cassette by recirculation of the admixture solution being formed. In particular, the arrangement includes a Y-set tubing assembly including first, second, and third tubing branches operatively joined by a Y-connector. The first tubing branch joins the liquid outlet of the pump cassette in fluid communication with the second and third branches. The second tubing branch joins an upstreammost one of the liquid inlets of the pump cassette in fluid communication with the first and third branches. Finally, the third tubing branch joins the admixture container in fluid communication with the first and second branches.

By this arrangement, compounding of liquid admixture in the container is effected by operating the positive displacement pump of the pump cassette to pump at least one source solution from a downstream one of the liquid inlets in the pump cassette through the liquid outlet and into the admixture container. During compounding, liquid flows from the pump cassette outlet through the first tubing branch, the Y-connector, and the third branch into the admixture container.

When the desired quantity of source solution has been drawn into the system from its respective liquid inlet, recirculation of the admixture through the pump cassette is effected. In this manner, the source solution concentrate in the system is delivered to the admixture container, with the admixture thereafter in the system ordinarily having the therapeutic agents carried therein in a sufficiently low concentration to avoid any undesirable precipitation with a source solution subsequently introduced into the system.

Notably, recirculation of the admixture through the pump cassette is effected by alternately:

(1) drawing the admixture from the container through the Y-set tubing assembly for flow into the upstreammost one of the liquid inlets; (2) and pumping liquid from the pump cassette through the Y-set assembly for flow into the admixture container. Thus, a flow path generally in the nature of a closed-loop is established so that the admixture is effectively recirculated through the pump cassette and associated tubing.

As will be appreciated, the admixture container functions in the nature of a reservoir during this recirculation sequence, with the method contemplating that flow through the second tubing branch and into the upstreammost inlet be from the container, and not merely from the first tubing branch extending from the liquid outlet. Accordingly, it will be appreciated that the predetermined maximum displacement volume of the positive displacement pump will be greater than the volume of the third branch of the Y-set tubing assembly, i.e., the branch joining the first and second branches in fluid communication with the admixture container.

Numerous other features and advantage of the present invention will become readily apparent from the following detailed description, the accompanying drawings, and the appended claims.

Figure 1:
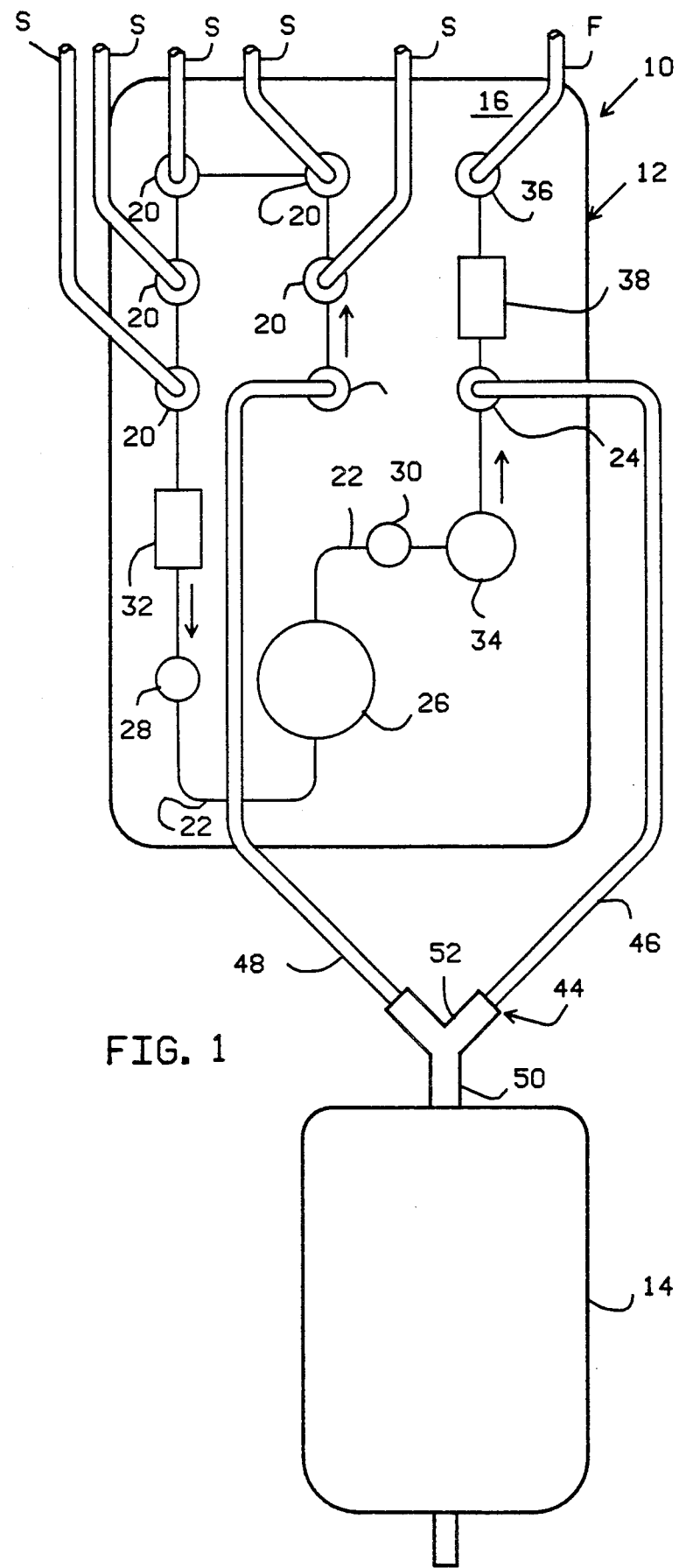
FIG. 1 is a diagrammatic view of an admixture compounding apparatus embodying the principles of the present invention.

While the present invention is susceptible of embodiment in various forms, there is shown in the drawings and will hereinafter be described a presently preferred embodiment, with the understanding that the present disclosure is to be considered as an exemplification of the invention, and is not intended to limit the invention to the specific embodiment illustrated.

With reference now to the drawing, therein is illustrated an admixture compounding apparatus 10 embodying the principles of the present invention. The compounding apparatus includes a pump cassette 12 which is configured for operation by an associated pump driver for effecting compounding of an admixture solution in a suitable admixture container 14. A particularly preferred embodiment for the pump cassette 12 is disclosed in greater detail in copending application Ser. No. 07/444,459, filed Dec. 1, 1989, and titled Solution Pumping System Including Disposable Pump Cassette. As will be recognized by those familiar with the art, some features of the compounding cassette 12 are similar to those
found in the pump cassette disclosed in U.S. Pat. No. 4,818,186, to Pastrone et al., and U.S. Pat. No. 4,842,584, to Pastrone, which patents are hereby incorporated by reference. While the disclosure of these patents particularly relates to a pump cassette and associated pump driver employed for infusion of parenteral solutions, many of the principles disclosed therein are equally applicable in connection with the present apparatus.

It is contemplated that the pump cassette 12 be configured for disposable use (such as on a daily basis), in the pharmacy of a health care facility, and thus includes a rigid cassette body 16 preferably formed from suitable thermoplastic material, such as polycarbonate. In the preferred form, the cassette body 16 includes plate-like front and rear body members which are joined together in confronting relation, with a flexible elastomeric diaphragm positioned therebetween. The pump cassette is preferably configured such that the front body member and the diaphragm together define the various inlets, outlet, and flow passages within the cassette, while the rear body member holds the diaphragm in tightly fitting and confronting relation against the front body member. Additionally, the rear body member defines a plurality of openings which expose the flexible diaphragm within the cassette. Flow control within the cassette is thus effected by suitable manipulation of the flexible diaphragm, through the openings in the rear body member. The diaphragm cooperates with the cassette body to provide a valve mechanism at each of the various inlets and at the liquid outlet of the cassette. The necessary selective deformation and relaxation of the diaphragm is effected by a plurality of solenoid-operated valve actuators, and a motor-driven pump plunger of the pump driver.

For compounding of parenteral admixtures, the pump cassette functions in the nature of a manifold through which various source solutions flow for compounding in admixture container 14. To this end, the pump cassette 12 includes a plurality of source solution liquid inlets 20, respectively joined to source solution tubing S, and a liquid flow path 22 for joining a selected one of the liquid inlets in fluid communication with a liquid outlet 24. Normal flow of liquid in the flow path, in the direction shown by the arrows, is effected by a positive displacement liquid pump 26.

The pump 26 includes a pump chamber defined by the front body member of the cassette body 16, and a portion of the diaphragm fitted in confronting relation with the pump chamber. Liquid flow is effected by reciprocation of the pump plunger of the associated pump driver against the diaphragm, in timed relation with operation of a selected upstream valve mechanism (such as at one of the inlets 20), and selected downstream valve mechanism (such as at outlet 24). A pump inlet valve 28 and a pump outlet valve 30 may optionally be provided for operation in timed relation with pump 26 to control liquid flow into and out of the pump chamber. However, it is presently preferred that such flow control be effected at a selected inlet and a selected outlet of the cassette while the inlet valve 28 and outlet valve 30 remain open. U.S. Pat. No. 4,639,245, to Pastrone et al., which is hereby incorporated by reference, discloses the general configuration of the positive displacement pump and associated reciprocable pump plunger. As will be appreciated, the liquid pump 26 can be operated to reverse liquid flow through the pump cassette, by reversing the sequence of operation of a selected liquid inlet and a selected liquid outlet relative to the reciprocation of the pump plunger of the associated driver.

Other features of the illustrated embodiment lend to the efficient and reliable operation of the present compounding apparatus in association with an automated compounding system.

An air sensor 32 is preferably provided for cooperation with a suitable detector mechanism on the associated pump driver, with the sensor 32 typically comprising a portion of the diaphragm which projects from the cassette body 16 so that the absence of source solution, or recirculated admixture, in the flow path 22 can be automatically detected.

The pump cassette 12 further includes a flush fluid inlet 36 joined in fluid communication with flow path 22 generally at liquid outlet 24, with the inlet 36 permitting introduction of flush fluid into the pump cassette for reverse flow therethrough. A flush fluid air sensor 38, configured like air sensor 32, facilitates automatic detection of the absence of flush fluid in the cassette flow path.

In accordance with the present invention, the pump cassette 12 further includes another liquid inlet 42 which is positioned upstream of the liquid inlets 20, and thus is the upstreammost one of the liquid inlets. Inlet 42 has been specifically provided to permit recirculation of the admixture solution from container 14 for effecting dilution of any undiluted source solution in the pump cassette 12. While the inlet 42 will be described herein as providing liquid flow into the cassette during recirculation of admixture, it will be appreciated that inlet 42 can further function as a liquid outlet, such as during flushing of the pump cassette with the liquid introduced into flush inlet 36.

In order to effect such recirculation with admixture solution, the present apparatus includes a Y-set tubing assembly 44 operatively joining liquid outlet 24, the liquid inlet 42, and the admixture container 14 in fluid communication with each other. Specifically, the Y-set tubing assembly includes first, second, and third tubing branches 46, 48, and 50, with the tubing branches joined together in fluid communication by a Y-connector 52. In accordance with the illustrated embodiment, first tubing branch 46 joins the liquid outlet 24 in fluid communication with the second and third tubing branches. The second tubing branch 48 joins the inlet 42 in fluid communication with the first and third tubing branches, while the third tubing branch 50 joins the admixture container 14 in fluid communication with the first and second tubing branches, via the Y-connector 52. In the preferred form, suitable manually operated clamps are provided on each of the first and second tubing branches for selectively closing the branches to liquid flow.

Use of the present apparatus in accordance with the method of the present invention for effecting recirculation of a liquid admixture through the pump cassette 12 will now be described. Preparation of the desired admixture, in accordance with a physician's order, is initiated by joining the admixture container 14 in fluid communication with the third tubing branch 50 of the Y-set tubing assembly, typically by "spiking" the needle typically provided on the Y-set assembly into the admixture container. Compounding of the liquid admixture is then initiated by operating the liquid pump 26 (by operation of the reciprocable pump plunger of the associated pump driver) to pump at least one source solution from one of the liquid inlets 20, arranged downstream of inlet 42, through the liquid outlet 24, and into the admixture container via the Y-set tubing assembly 44.

After the desired quantity of the source solution has been received through the selected inlet 20, the respectively associated one of the valve actuators of the pump driver is operated to close that inlet. Recirculation in accordance with the present invention is now effected. Specifically, inlet 42 and outlet 24 are alternately opened and closed, and the liquid pump 26 operated so that liquid flows from outlet 24 and through first and third tubing branches 46 and 50 and into admixture container 14, while admixture solution is drawn from the admixture container, through the third and second tubing branches 50 and 48, and into the upstreammost liquid inlet 42. Thus, the liquid pump alternately draws admixture from the container for flow into the inlet 42, and pumps liquid from outlet 24 of the pump cassette through the Y-set tubing arrangement for flow into the container. Pumping is continued for a sufficient period of time so as to recirculate the admixture being formed completely through the flow path of the pump cassette, thereby diluting any relatively undiluted source solution in the pump cassette with the admixture.

As will be appreciated, when the present invention is configured in accordance with the preferred embodiment, including the Y-set tubing assembly 44, certain volumetric relationships are required in the arrangement to ensure that admixture is drawn from container 14 for recirculation into the pump cassette 12 via inlet 42. Specifically, the pump 26 has a predetermined maximum displacement volume which is greater than the volume of the third branch 50 of the Y-set tubing assembly 44. This third branch volume includes any interior volume of the Y-connector 52 which joins the third branch 50 with the first and second branches 46 and 48. This assures that admixture is drawn from the container 14 and into the second tubing branch 48 for eventual flow to inlet 42 during the return or filling stroke of the pump. As will be appreciated, this preferred relationship would not be necessary in an embodiment of the present invention not including the Y-set tubing assembly, but instead, merely including individual and separate tubing connections between each of outlet 24 and inlet 42 and the admixture container 14.

Ordinarily, compounding of the desired admixture includes operation of the pump 26, and the associated source solution inlets 20, to selectively pump each of a plurality of different source solutions from respective ones of the inlets 20. Accordingly, in order to avoid the undesired mixing of incompatible source solutions, it is contemplated that the above-described recirculation of admixture be effected after pumping of each of the selected ones of the source solutions.

As will be appreciated, the above-described method acts to flush any undiluted source solution from the pump cassette, and associated tubing, to thereby prevent precipitation should an incompatible source solution be dispensed after the recirculation. The present method is also intended to transfer the majority of the selected source solution that is in the tubing assembly into the admixture container 14. The above-described admixture recirculation is also preferably effected at the conclusion of the admixture preparation to ensure that the last-selected source solution is transferred to the admixture container and not left in the associated tubing.

The above-described recirculation may be followed by flushing of the pump cassette 12 with flush fluid, such as sterile water. This flush fluid is introduced into the cassette via inlet 36, and is intended to push any remaining admixture out of the Y-set tubing assembly 44 and into the admixture container 14. The use of sterile water or other suitable neutral solution is desired since a small amount of the sterile water is introduced into the admixture container 14.

Flushing in this manner is effected by closing outlet 24 by appropriate operation of their respective valve actuator of the associated pump driver. Upstreammost inlet 42 and the flush fluid inlet 36 are then alternately opened and closed in the desired timed relation to operation of pump 26 so that flush fluid introduced into inlet 36 flows in reverse direction through the liquid flow path 22 to the inlet 42. Pumping in this manner may continue if it is desired to further flush second and third tubing branches 48 and 50.

If flushing of the first tubing branch 46 is to then be effected, pump 26 can be operated to alternately draw flush fluid in through inlet 36, and to pump the flush fluid out through outlet 24 and into first tubing branch 46. Specifically, inlet 42 is closed, and with pump outlet valve 30 open, flush fluid inlet 36 and outlet 24 are alternately opened and closed in synchronization with stroking of the pump 26 by the associated reciprocable pump plunger. Since the volume of the flow path 22 between flush fluid inlet 36 and the pump 26 is preferably smaller than the maximum displacement volume of the pump, operation in this manner acts to draw fluid in through the inlet 36 (when it is open and outlet 24 is closed), and thereafter force the flush fluid out outlet 24, after it is opened and inlet 36 is closed.

From the foregoing, it will be observed that numerous modification and variations can be effected without departing from the true spirit and scope of the novel concept of the present invention. It is to be understood that no limitation with respect to the specific embodiment illustrated herein is intended or should be inferred. The disclosure is intended to cover by the appended claims all such modifications as fall within the scope of the claims.

What is claimed is:

1. A method of compounding a liquid admixture using a pump cassette having a plurality of liquid inlets joined in fluid communication with a liquid outlet via a liquid flow path, and positive displacement pump means for pumping liquid from a selected one of said inlets to said outlet, said method comprising the steps of:
   providing an admixture container;
   providing liquid tubing means for joining said liquid outlet and an upstreammost one of said liquid inlets in fluid communication with said admixture container;
   compounding a liquid admixture in said admixture container by operating said pump means to pump at least one source solution from a downstream one of said liquid inlets through said liquid outlet and into said admixture container; and
   selective recirculating said liquid admixture through said pump cassette.

2. A compounding method in accordance with claim 1, wherein
   said recirculating step comprises alternate steps of: drawing said admixture from said container through said tubing means for flow into said upstreammost liquid inlet; and
   pumping liquid from said pump cassette through said tubing means for flow into said admixture container.

3. A compounding method in accordance with claim 2, wherein
   said liquid tubing means comprises a Y-set tubing assembly including first, second, and third tubing branches, said first tubing branch joining said liquid outlet in fluid communication with said second and third tubing branches, said second tubing branch joining said upstreammost liquid inlet in fluid communication with said first and third tubing branches, and said third tubing branch joining said admixture container in fluid communication with said first and second tubing branches.

4. A compounding method in accordance with claim 3, wherein
   said positive displacement pump means has a predetermined maximum displacement volume, said maximum displacement volume being greater than the volume of said third branch of said Y-set tubing assembly.

5. A compounding method in accordance with claim 1, wherein
   said compounding step includes operating said pump means to selectively pump each of a plurality of source solutions from respective downstream ones of said liquid inlets,
   said recirculating step, including recirculating the liquid admixture being formed through said pump cassette after pumping of each of said source solutions.

6. A compounding method in accordance with claim 1, including
   flushing said pump cassette with a flush fluid introduced into a fluid inlet disposed in fluid communication with said liquid flow path downstream of said liquid outlet, and reversibly operating said positive displacement pump means so that said flush fluid flows through said flow path and out of said upstreammost inlet.

7. An apparatus for compounding an admixture solution, comprising:
   a pump cassette including a plurality of liquid inlets, a liquid outlet, a liquid flow path joining said inlets and said outlet in fluid communication, and positive displacement pump means for pumping liquid from a selected one of said inlets to said outlet;
   an admixture container for receiving at least one source solution from said pump cassette for forming an admixture solution; and
   recirculation means comprising means for joining said outlet and an upstreammost one of said inlets in fluid communication with said admixture container, whereby said pump means is selectively operable to alternately: draw said admixture from said container and into said recirculation means for flow into said one inlet; and pump liquid from said cassette through said recirculation means for flow into said admixture container.

8. An apparatus for compounding an admixture in accordance with claim 7, wherein
   said recirculation means comprises a Y-set tubing assembly including first, second, and third tubing branches, said first tubing branch joining said liquid outlet in fluid communication with said second and third tubing branches, said second tubing branch joining said one liquid inlet in fluid communication with said first and third tubing branches, and said third tubing branch joining said admixture container in fluid communication with said first and second tubing branches.

9. An apparatus for compounding an admixture in accordance with claim 8, wherein
   said positive displacement pump means has a predetermined maximum displacement volume which is greater than the volume of said third branch of said Y-set tubing assembly.

* * * * *

UNITED STATES PATENT AND TRADEMARK OFFICE
CERTIFICATE OF CORRECTION

PATENT NO. : 5,082,014
DATED : Jan. 21, 1992
INVENTOR(S) : MICHAEL D. OLICHNEY

It is certified that error appears in the above-identified patent and that said Letters Patent is hereby corrected as shown below:

Column 7, line 46: Replace "selective" with --selectively--

Signed and Sealed this

Twenty-eighth Day of September, 1993

*Attest:*

BRUCE LEHMAN

*Attesting Officer*  *Commissioner of Patents and Trademarks*